United States Patent
Hamaguchi et al.

(10) Patent No.: US 9,791,373 B2
(45) Date of Patent: Oct. 17, 2017

(54) METHOD FOR QUANTITATIVE SPECTROMETRY, QUANTITATIVE SPECTROMETRY APPARATUS, AND PROGRAM

(71) Applicant: Spectroscopic Science Laboratory Co., Ltd., Kawasaki-shi, Kanagawa (JP)

(72) Inventors: Hiro-o Hamaguchi, Kawasaki (JP); Masahiro Ando, Kawasaki (JP)

(73) Assignee: SPECTROSCOPIC SCIENCE LABORATORY CO., LTD., Kawasaki-Shi (JP)

(*) Notice: Subject to any disclaimer, the term of this patent is extended or adjusted under 35 U.S.C. 154(b) by 0 days.

(21) Appl. No.: 15/312,488

(22) PCT Filed: Aug. 26, 2015

(86) PCT No.: PCT/JP2015/073944
§ 371 (c)(1),
(2) Date: Nov. 18, 2016

(87) PCT Pub. No.: WO2016/035626
PCT Pub. Date: Mar. 10, 2016

(65) Prior Publication Data
US 2017/0131212 A1   May 11, 2017

(30) Foreign Application Priority Data
Sep. 5, 2014   (JP) ................. 2014-180885

(51) Int. Cl.
*G01N 21/65* (2006.01)
*G01N 21/31* (2006.01)
(Continued)

(52) U.S. Cl.
CPC ............ *G01N 21/65* (2013.01); *G01N 33/49* (2013.01); *G01N 2201/12* (2013.01)

(58) Field of Classification Search
CPC ........ G01N 21/65; G01N 21/64; G01N 21/35; G01N 21/33; G01N 21/31; G01N 21/27; G01N 24/08
See application file for complete search history.

(56) References Cited

U.S. PATENT DOCUMENTS 5,886,347 A   3/1999   Inoue et al.
2007/0184455 A1   8/2007   Arrowsmith et al.

FOREIGN PATENT DOCUMENTS

JP   8-29332   2/1996
JP   2003-035662   2/2003
(Continued)

OTHER PUBLICATIONS

Bhaskar et al., Multivariate Chemometric Assisted Analysis of Metformin Hydrochloride, Gliclazide and Pioglitazone Hydrochloride in Bulk Drug and Dosage Forms, ePublished: Feb. 7, 2013, Advanced Pharmaceutical Bulletin, 3(1), pp. 79-84.*
International Search Report, dated Nov. 24, 2015 (Nov. 24, 2015).

*Primary Examiner* — Toan Le
(74) *Attorney, Agent, or Firm* — Rankin, Hill & Clark LLP

(57) ABSTRACT

A composition ratio of a component targeted for quantification in a liquid, solid, or gaseous mixture is determined without taking the effort of performing measurement while stepwise changing an addition concentration as in an existing standard addition method. A quantitative spectrometry apparatus 100 includes a measurement unit 110 that spectroscopically analyzes an analysis-target sample 10 containing a component targeted for quantification in an unknown composition ratio and a reference sample containing the component targeted for quantification in a known composition ratio to obtain an original spectrum and a reference spectrum, a first generation unit 130 that generates, from these spectra, hypothetical addition spectra including a plu-
(Continued)

rality of hypothetical addition rates as coefficients, a second generation unit that generates a plurality of analysis-target spectra from the respective hypothetical addition spectra, an extraction unit 170 that extracts a signal intensity profile of the component targeted for quantification corresponding to the hypothetical addition rates by performing a process including multivariate analysis, and a determination unit 190 that determines the unknown composition ratio of the component targeted for quantification contained in the analysis-target sample 10 from the dependence of the signal intensity profile on the hypothetical addition rates.

20 Claims, 13 Drawing Sheets

(51) Int. Cl.
*G01N 21/27* (2006.01)
*G01N 33/49* (2006.01)

(56) References Cited

FOREIGN PATENT DOCUMENTS

| | | |
|---|---|---|
| JP | 2003-035663 | 2/2003 |
| JP | 2003-042949 | 2/2003 |
| JP | 2010-520471 | 6/2010 |
| JP | 4897110 | 1/2012 |
| WO | 2008/107465 | 9/2008 |

* cited by examiner

FIG. 17

[Math. 1]

$$A = \begin{pmatrix} \text{analysis-target spectrum (1)} & \text{analysis-target spectrum (2)} & \cdots & \text{analysis-target spectrum (N)} \end{pmatrix} = W \cdot H$$

(N columns), (M rows)

FIG. 18

[Math. 2]

$$W = \begin{pmatrix} \text{first component spectrum} & \text{second component spectrum} \end{pmatrix}$$

(M rows)

FIG. 19

[Math. 3]

$$H = \begin{bmatrix} \overset{\longleftarrow \text{(N columns)} \longrightarrow}{\text{first component intensity profile}} \\ \text{second component intensity profile} \end{bmatrix}$$

US 9,791,373 B2

METHOD FOR QUANTITATIVE SPECTROMETRY, QUANTITATIVE SPECTROMETRY APPARATUS, AND PROGRAM

TECHNICAL FIELD

The present invention relates to a method for quantitative spectrometry, a quantitative spectrometry apparatus, and a program, and more specifically to a technique for determining an unknown composition ratio of a component targeted for quantification in a mixture by using spectroscopic analysis.

BACKGROUND ART

A standard addition method is known as a method for finding out the proportion (composition ratio) of a specific component contained in a mixture made by mixing diverse components. In the following, a description is given taking a solution as an example. In the standard addition method, in order to know an unknown composition ratio (concentration) of a specific component (hereinafter referred to as a component targeted for quantification) in a solution sample, a component identical to the component targeted for quantification is used as a solute and is added to the sample stepwise with the concentration of the component being changed.

Signal intensities obtained by applying spectrometry to the sample in the case where the concentration of the solute added is zero and in the respective cases where the concentration of the solute added increases stepwise are plotted with respect to the solute-addition concentration, thereby enabling a so-called calibration curve to be obtained. The calibration curve can be approximated substantially linearly, and thus can be extrapolated to a range within which the solute-addition concentration has negative values to enable determination of an addition concentration of a negative value which corresponds to a signal intensity value of zero. The absolute value of the determined value is equal to the unknown concentration before the addition of the component targeted for quantification is started. In this way, the unknown concentration of the component targeted for quantification can be found out (see, for example, PTL 1).

PTL 1, noted above, describes a method in which the concentration of carbon having specific bonds that bring a preferable effect to the properties of an electrode catalyst, which is used for a fuel cell or the like, in the catalyst is determined by Raman spectroscopy. Specifically, a method is presented in which the target sample to be quantified is split into four or more containers and a component identical to the component targeted for quantification, called furnace black, is added to each of the containers in differing concentrations to prepare a relation curve between the Raman spectroscopic intensity and the concentration.

While the Raman spectroscopic analysis is used as spectroscopic analysis in PTL 1, the type of spectroscopic analysis available in the standard addition method is not limited to the Raman spectroscopic analysis. An appropriate type of spectroscopic analysis is selectable on a case-by-case basis taking into account conditions such as the properties of the object to be measured, the required measurement accuracy, and the availability of measurement facilities.

However, existing standard addition methods (including the method described in PTL 1) are designed to add a component identical to the component targeted for quantification to the sample stepwise and to perform spectroscopic measurement and analysis each time the component is added to the sample, and thus have drawbacks of being labor-intensive and taking a comparatively long time. The existing standard addition methods also have a drawback of being typically difficult to apply when the sample is a solid.

CITATION LIST

Patent Literature

PTL 1: Japanese Patent No. 4897110 (paragraph "0043")

SUMMARY OF INVENTION

Technical Problem

In the existing standard addition methods, it is common to use a signal intensity of a specific wavelength that shows a notable reaction in the spectrometry. This results in much of information obtained along the wavelength axis (spectral axis) as a result of the spectrometry being disposed of without being used. It is an object of the present invention not to dispose of but to use such information to determine an unknown composition ratio of a specific component in a mixture, regardless of whether it is a liquid, solid, or gas, while compensating for the above-described drawbacks of existing standard addition methods.

Solution to Problem

To achieve the object described above, a method for quantitative spectrometry according to the present invention is a method capable of quantifying a composition ratio of a component targeted for quantification that is contained in an analysis-target sample by using spectroscopic analysis, the analysis-target sample containing the component targeted for quantification and a component not targeted for quantification, the method including measuring an original spectrum from the analysis-target sample by using the spectroscopic analysis, the analysis-target sample containing the component targeted for quantification in an unknown composition ratio; multiplying a reference spectrum by a plurality of hypothetical addition rates, the reference spectrum being measured by using the spectroscopic analysis from a reference sample containing the component targeted for quantification in a known composition ratio, and adding the respective hypothetical addition rate-multiplied reference spectra to the original spectrum, thereby generating a plurality of hypothetical addition spectra; generating a plurality of analysis-target spectra from the plurality of hypothetical addition spectra; extracting a signal intensity profile of the component targeted for quantification corresponding to the hypothetical addition rates from the plurality of analysis-target spectra by using multivariate analysis; and determining the unknown composition ratio of the component targeted for quantification from a dependence of the extracted signal intensity profile on the hypothetical addition rates.

Furthermore, a quantitative spectrometry apparatus according to the present invention is an apparatus capable of quantifying a composition ratio of a component targeted for quantification that is contained in an analysis-target sample by using spectroscopic analysis, the analysis-target sample containing the component targeted for quantification and a component not targeted for quantification, the apparatus including a measurement unit capable of measuring an original spectrum from the analysis-target sample by using the spectroscopic analysis, the analysis-target sample containing the component targeted for quantification in an unknown composition ratio, a first generation unit capable of multiplying a reference spectrum by a plurality of hypothetical addition rates, the reference spectrum being measured by using the spectroscopic analysis from a reference sample containing the component targeted for quantification in a known composition ratio, and adding the respective hypothetical addition rate-multiplied reference spectra to the original spectrum, thereby generating a plurality of hypothetical addition spectra, a second generation unit capable of generating a plurality of analysis-target spectra from the plurality of hypothetical addition spectra, an extraction unit capable of extracting a signal intensity profile of the component targeted for quantification corresponding to the hypothetical addition rates from the plurality of analysis-target spectra by using multivariate analysis, and a determination unit capable of determining the unknown composition ratio of the component targeted for quantification from a dependence of the extracted signal intensity profile on the hypothetical addition rates.

Advantageous Effects of Invention

According to the present invention, it is achievable to effectively use information obtained along the spectral axis as a result of spectrometry to determine an unknown composition ratio of a specific component in a mixture, regardless of whether it is a liquid, solid, or gas, while compensating for the drawbacks of existing standard addition methods. It is also achievable to simultaneously determine composition ratios of a plurality of components targeted for quantification by simultaneous generation and analysis of hypothetical addition spectra for the plurality of components targeted for quantification.

BRIEF DESCRIPTION OF DRAWINGS

FIG. 17 is an expression defining a product comprising a matrix of M rows and N columns.

FIG. 18 is an expression defining a first component spectrum and a second component spectrum in matrix form.

FIG. 19 is an expression defining a first component intensity profile and a second component intensity profile in matrix form. (Example 3).

DESCRIPTION OF EMBODIMENTS

Examples of the present invention will be described hereinafter with reference to the drawings.

Example 1

Figure 1:
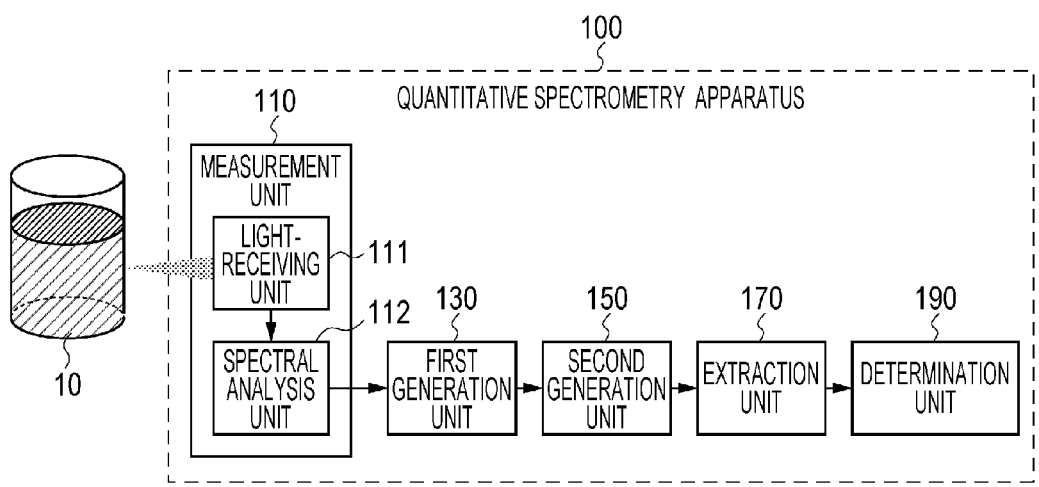
FIG. 1 is a system diagram illustrating a configuration of a quantitative spectrometry apparatus (Example 1).

Example 1 of the present invention will be described with reference to FIGS. 1 to 10. FIG. 1 is a system diagram illustrating a configuration of a quantitative spectroscopic apparatus 100 according to Example 1 of the present invention. An analysis-target sample 10 is illustrated in the left part of FIG. 1. The analysis-target sample 10 is, for example, an aqueous mixed solution of glucose, sucrose, and fructose. Among them, in Example 1, glucose is assumed to be a component targeted for quantification whose composition ratio (concentration) is unknown. In order to assess the effect of Example 1 (a determination error of the unknown concentration based on the present invention), the analysis-target sample 10 is prepared with a glucose concentration true value of 1.05% and the following steps are performed assuming that the true value is unknown.

The quantitative spectroscopic apparatus 100 includes configuration elements within an area enclosed by a dashed line in FIG. 1. The configuration elements are a measurement unit 110, a first generation unit 130, a second generation unit 150, an extraction unit 170, and a determination unit 190. The configuration elements described above are implementable by using various means including hardware or software, as described below, and do not always restrictively mean the presence of hardware or software blocks that are clearly defined in the manner as identified as the respective configuration elements described above.

The measurement unit 110 includes a light-receiving unit 111 that receives light transmitted through the analysis-target sample 10 or scattered from the analysis-target sample 10, and a spectral analysis unit 112 that analyzes spectra of the received light (the "light", as used herein, refers to light or electromagnetic waves used in the method for spectroscopic analysis. The term spectroscopic analysis, as used herein, refers to spectroscopic analysis in general, including ultraviolet-visible absorption spectroscopic analysis, fluorescence spectroscopic analysis, phosphorescence spectroscopic analysis, atomic absorption spectroscopic analysis, infrared absorption spectroscopic analysis, Raman spectroscopic analysis, X-ray spectroscopic analysis, nuclear magnetic resonance analysis, electron-spin resonance analysis, and microwave analysis). In some cases, the measurement unit 110 includes a light-emitting unit (not illustrated) in addition to the light-receiving unit 111 depending on the type of the spectroscopic analysis to be used.

The measurement unit 110 is assumed to use the Raman spectroscopic analysis, for example. In this case, the measurement unit 110 includes a light-emitting unit (not illustrated), and the light-emitting unit and the light-receiving unit 111 are configured to correspond to an optical system for various commercially available Raman spectrometers (the details of which are omitted here). The spectral analysis unit 112 is capable of analyzing Raman scattered light received by the light-receiving unit 111 and of plotting a spectrum of the Raman scattered light on a plane with Raman shift values on one axis (typically, the horizontal axis) and light intensity values on the other axis (typically, the vertical axis). The axis representing the Raman shift is a type of axis (called a spectral axis) representing the wave number, wavelength, or frequency of the light.

The measurement unit 110 having the configuration described above is capable of obtaining Raman scattered light from the analysis-target sample 10, which contains glucose, or a component targeted for quantification, in an unknown concentration, and of measuring a spectrum of the received light in the way described above. The spectrum of the analysis-target sample 10 is referred to as an original spectrum. The measurement unit 110 is also capable of obtaining Raman scattered light from a reference sample (for example, an aqueous solution) containing glucose in a known concentration and from its solvent in a similar manner and of performing a process described below to measure the spectrum of glucose alone. This spectrum is referred to as a reference spectrum.

The first generation unit 130 is implemented by software incorporated in a personal computer (PC), for example, and is capable of performing a computation process with the original spectrum and the reference spectrum as input, as described below, to generate a plurality of spectra called hypothetical addition spectra (including parameters called hypothetical addition rates).

The second generation unit 150 is implemented by software incorporated in a PC, for example, and is capable of performing a computation process with the plurality of hypothetical addition spectra as input, as described below, to generate a plurality of spectra called analysis-target spectra.

The extraction unit 170 is implemented by software incorporated in a PC, for example, and is capable of performing a process including multivariate analysis with the plurality of analysis-target spectra as input, as described below, to extract a signal intensity profile of the component targeted for quantification corresponding to the hypothetical addition rates.

The determination unit 190 is implemented by software incorporated in a PC, for example, and is capable of determining, as described below, an unknown composition ratio of the component targeted for quantification (for example, the concentration of glucose) contained in the analysis-target sample 10 from the dependence of the extracted signal intensity profile on the hypothetical addition rates.

Figure 2:
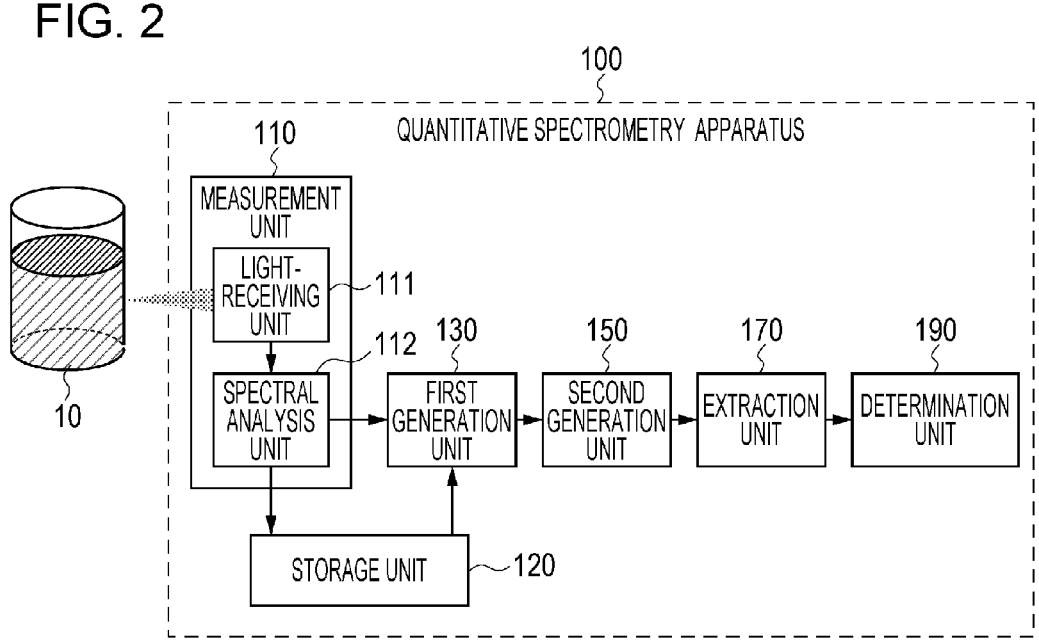
FIG. 2 is a system diagram illustrating a modified configuration of the quantitative spectrometry apparatus (Example 1).

As illustrated in FIG. 2, the quantitative spectrometry apparatus 100 may further include a storage unit 120. The storage unit 120 is capable of storing data of the reference spectrum measured by the measurement unit 110 and reading and providing the stored data of the reference spectrum to the first generation unit 130. A specific configuration of the quantitative spectrometry apparatus 100 is not limited to that described above. Each portion may be implemented in hardware or firmware mainly or in any combination of hardware or firmware and software. Alternatively, a program according to the present invention may be installed into a commercially available spectrometer.

Figure 3:
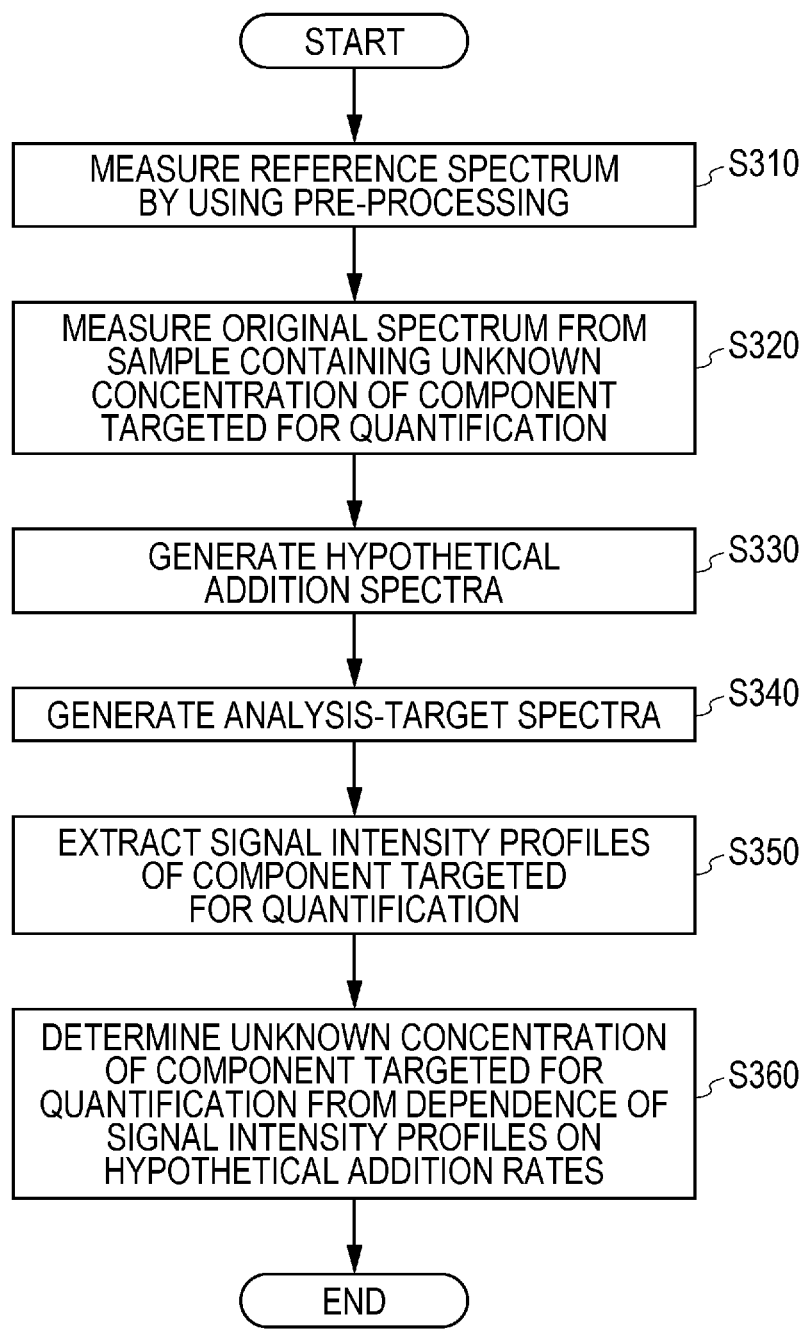
FIG. 3 is a flowchart illustrating a method for quantitative spectrometry (Example 1).

A method for quantitative spectrometry performed by using the quantitative spectrometry apparatus 100 according to Example 1 will be described with reference to FIGS. 3 to 10. FIG. 3 is a flowchart illustrating the method for quantitative spectrometry. The analysis-target sample 10 is a mixture (solution) containing glucose, which is a component targeted for quantification, in an unknown concentration, and an object of performing the method for quantitative spectrometry is to determine the unknown concentration.

Figure 4:
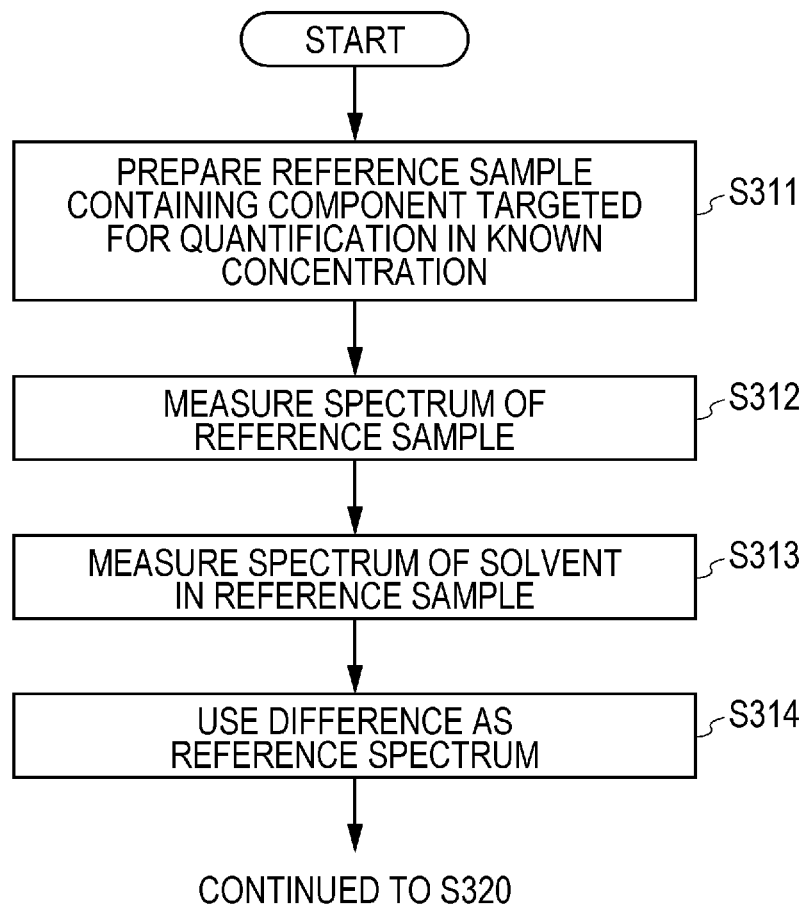
FIG. 4 is a sub-flowchart illustrating the details of pre-processing in FIG. 3 (Example 1).
Figure 5:
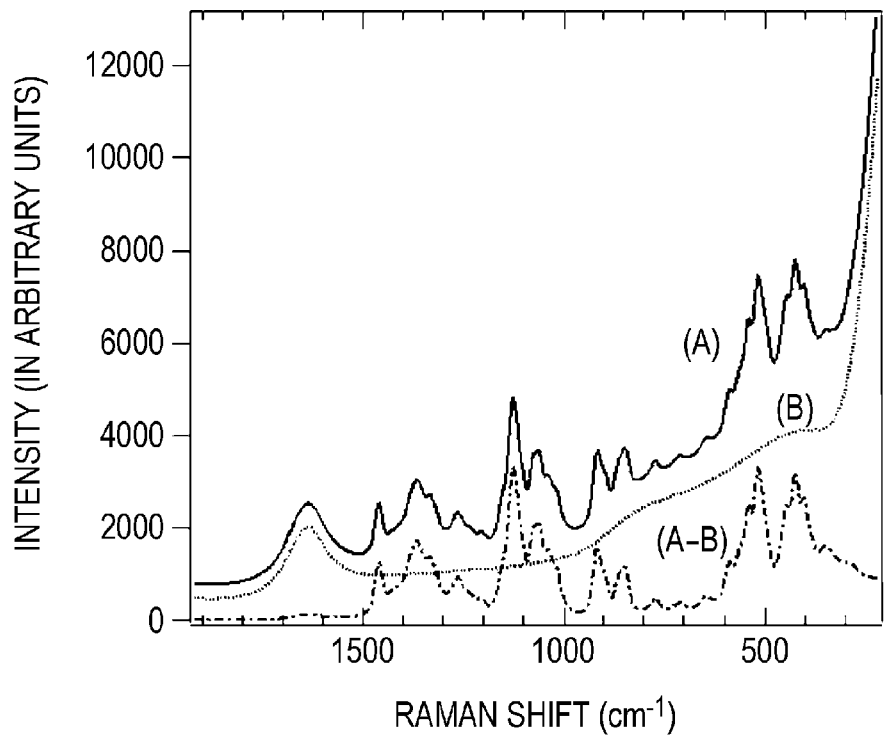
FIG. 5 is a chart illustrating an example of spectra measured in the pre-processing (Example 1).

After the start of the operation (START), first, pre-processing is performed. The pre-processing is a step (S310) of measuring a reference spectrum from a reference sample with glucose, which is a component targeted for quantification. FIG. 4 is a sub-flowchart illustrating a method for the pre-processing (step S310 in FIG. 3) according to Example 1. FIG. 5 is a chart illustrating an example of spectra measured in the pre-processing, with the horizontal axis representing the Raman shift (the units being $cm^{-1}$) and the vertical axis representing the light intensity (in arbitrary units).

First, a reference sample containing glucose, which is a component targeted for quantification, in a known concentration (for example, an aqueous solution having a concentration of 10%) is prepared (step S311). Then, a spectrum of the prepared reference sample is measured by using the measurement unit 110 of the quantitative spectrometry apparatus 100 (step S312; solid-line plot (A) in FIG. 5). The spectrum measured here includes a spectrum of the Raman scattered light of glucose, which is a solute, and a spectrum of scattered or radiated light derived from the solvent.

Subsequently, a spectrum of a component (for example, water) identical to the solvent (not containing glucose) used for the reference sample is measured by using the measurement unit 110 of the quantitative spectrometry apparatus 100 (step S313; dotted-line plot (B) in FIG. 5). As a result, a spectrum of scattered or radiated light derived only from the solvent is measured. The difference between the spectrum obtained in step S312 and the spectrum obtained in step S313 is taken to obtain a spectrum of the Raman scattered light of glucose contained in the reference sample in the known concentration. The spectral analysis unit 112 inputs this spectrum to the first generation unit 130 as a reference spectrum (step S314; one-dot chain line plot (A)-(B) in FIG. 5).

Here, the reference spectrum was measured by using an aqueous solution of glucose to be a reference sample. The reason for this resides in the necessity for a spectrum of glucose in an aqueous solution to be used as a reference spectrum in order to determine the concentration of glucose in the analysis-target sample (liquid) (pure glucose is a solid having a molecular structure different from that when glucose is present in a solution and exhibiting a different spectrum). In contrast, when the component targeted for quantification is in a pure state and is present as a liquid, in order to determine the concentration of this component in the analysis-target sample (liquid), the component targeted for quantification (100% concentration) itself is used as a reference sample and its spectrum is directly measured and can be used as a reference spectrum.

It is assumed that the quantitative spectrometry apparatus 100 includes the storage unit 120 in the manner as illustrated in FIG. 2. In this case, data of a reference spectrum obtained by performing the pre-processing (step S310) once for each type of component targeted for quantification is stored in the storage unit 120, and this data is read, when necessary, and input to the first generation unit 130. This can eliminate the pre-processing when an unknown concentration is to be subsequently quantified.

Referring back to FIG. 3, a spectrum of the analysis-target sample 10 is measured by using the measurement unit 110 (step S320). The spectral analysis unit 112 inputs the obtained spectrum to the first generation unit 130 as an original spectrum. The first generation unit 130 multiplies the earlier input reference spectrum by a plurality of coefficients, and adds each of the coefficient-multiplied reference spectra to the original spectrum (step S330).

In the current case, the reference spectrum was the spectrum of the glucose component extracted from the spectrum of the aqueous solution of glucose having a concentration of 10%. Thus, the process of multiplying the reference spectrum by coefficients and adding each of the coefficient-multiplied reference spectra to the original spectrum can be equivalent to that in which a standard addition method for adding the component targeted for quantification to the sample in real space while stepwise changing the concentration of the component targeted for quantification is performed in spectral space in a hypothetical fashion. Accordingly, the coefficients described above are called hypothetical addition rates and the resulting plurality of spectra are called hypothetical addition spectra.

Figure 6:
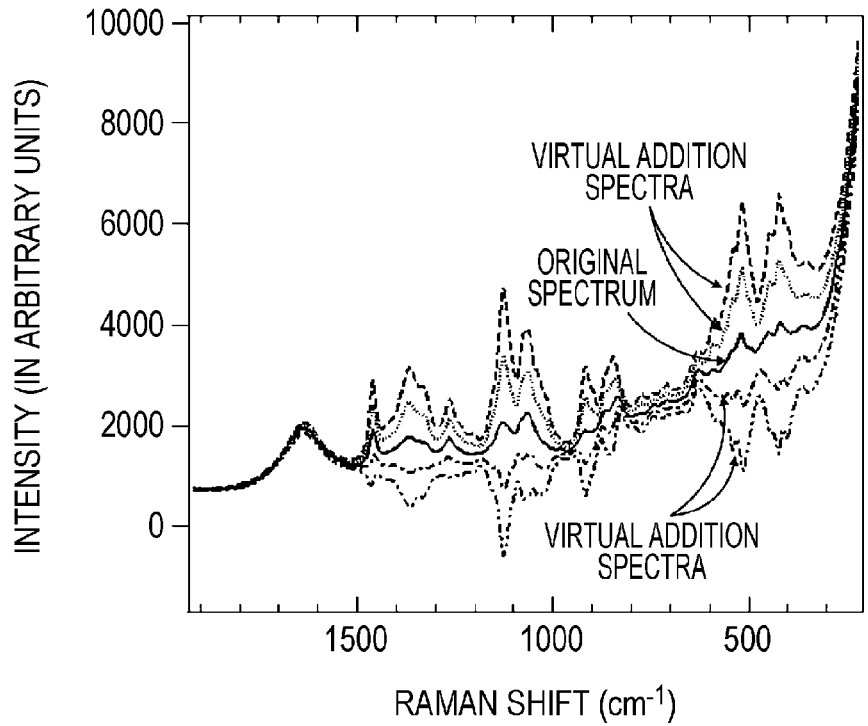
FIG. 6 is a chart illustrating, by way of example, an original spectrum and hypothetical addition spectra (Example 1).

FIG. 6 is a chart illustrating, by way of example, the original spectrum measured from the analysis-target sample 10 and the hypothetical addition spectra described above. A solid line near the middle represents the original spectrum and upper and lower lines of types different from the solid line represent the plurality of hypothetical addition spectra. While the horizontal axis and the vertical axis correspond to those in FIG. 5, any positive and negative values are permissible as hypothetical addition rates and hence the numerical range of vertical axis values contains both positive and negative values.

The first generation unit 130 inputs the plurality of hypothetical addition spectra described above to the second generation unit 150. The second generation unit 150 performs a differentiation operation one or more times on each of the hypothetical addition spectra along the spectral axis (in the case illustrated in FIG. 6, along the horizontal axis representing the Raman shift). In the original spectrum included in the hypothetical addition spectra, as illustrated by way of example in FIG. 6, the contribution of background signals due to autofluorescence of a component contained in the analysis-target sample 10 or stray light such as room light is dominant. If the background signals have a feature of changing by a small amount or changing slowly over a wide range along the spectral axis, in order to extract the contribution of glucose showing abrupt changes but exhibiting a relatively small amplitude along the vertical axis from the contribution of the background signals, it is effective to perform a differentiation operation one or more times to reduce the contribution of the background signals. The differentiation operations described above may be omitted depending on the properties of the background signals or any other condition.

Figure 7:
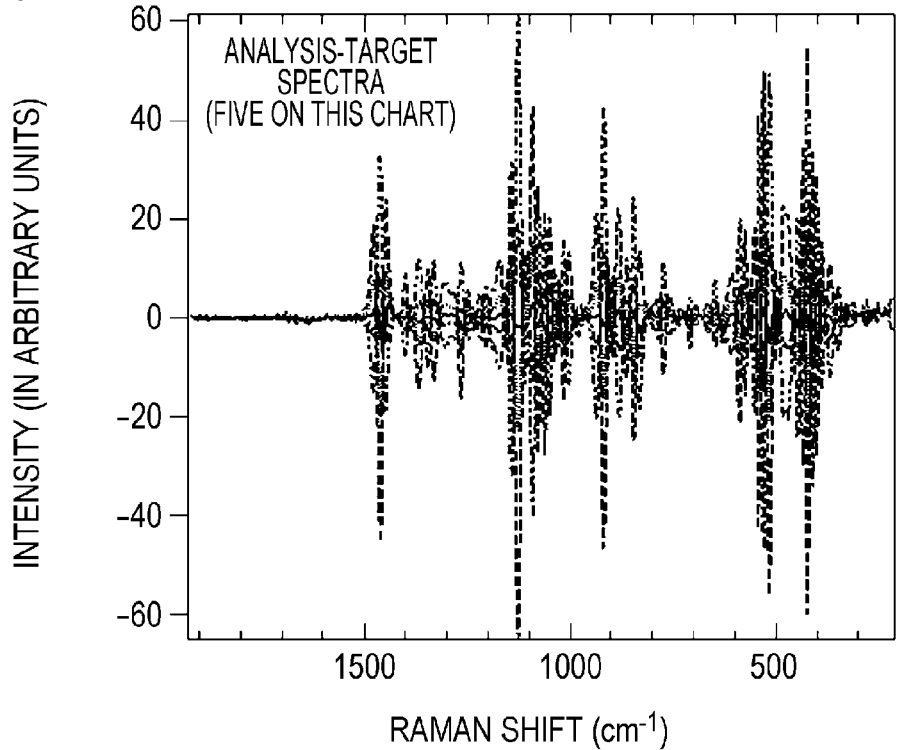
FIG. 7 is a chart illustrating, by way of example, a plurality of analysis-target spectra (Example 1).

The differentiation operations can be performed one or more times on the hypothetical addition spectra illustrated in FIG. 6 (step S340) to obtain a plurality of spectra to be subjected to analysis for determining an unknown concentration of glucose contained in the analysis-target sample 10. These spectra are referred to as analysis-target spectra (as described above, the differentiation operations may be omitted depending on the condition and the hypothetical addition spectra may be used directly as analysis-target spectra). The hypothetical addition spectra illustrated by way of example in FIG. 6 are differentiated twice, for example, along the spectral axis to obtain a plurality of (on this chart, five) analysis-target spectra which are illustrated in FIG. 7 (a chart depicting five spectra, as in FIG. 6).

The operations in steps S330 and S340 described above are described below using mathematical expressions. The reference spectrum and the original spectrum are respectively represented by vectors Sref and Sorg, each having elements specifying the respective signal intensities at a plurality of (for example, M) discrete points (pixels) on the spectral axis. The hypothetical addition rates are represented by N scalars Cj (j is an integer from 1 to N), for example, and hypothetical addition spectra including Cj as coefficients are represented by vectors S(j). This yields the equation $$S(j) = Sorg + Cj \times Sref,$$

where Cj can take any real number value of being either positive or negative.

In this Example, the second generation unit 150 differentiates the hypothetical addition spectra S(j) one or more times along the spectral axis. In the current case, differentiation is performed twice on the basis of the properties of the background signals of the original spectrum seen in FIG. 6. The second generation unit 150 inputs the resulting analysis-target spectra to the extraction unit 170 as vectors $S2(j)$. The extraction unit 170 horizontally arranges column vectors $S2(j)^T$, each obtained by vertically arranging the elements corresponding to M pixels for $S2(j)$, in the order of the values of j starting from 1 to N to obtain a matrix of M rows and N columns. This matrix is represented by a sign A. The matrix A is obtained by arranging column vectors equivalent to a plurality of analysis-target spectra obtained with a plurality of varying values of the hypothetical addition rate, and can thus be construed as being equivalently constituted by (spectra corresponding to the contribution of part of Raman scattered light that relatively abruptly changes among) spectra each measured by using the standard addition method each time the addition concentration is changed.

The analysis-target sample 10 is considered to be separated into a component other than glucose, which is a component not targeted for quantification, and glucose, which is a component targeted for quantification, the component not targeted for quantification being called a first component and the component targeted for quantification being called a second component. If respective Raman spectra in the presence of the first component alone and the second component alone (the respective Raman spectra being respectively called a first component spectrum and a second component spectrum) can be individually determined, the (i, j) element of the matrix A described above can be determined by adding together a value obtained by multiplying the i-th element of the first component spectrum by the j-th element of the signal intensity profile (hereinafter referred to as intensity profile) of the first component along the value axis of the hypothetical addition rate and a value obtained by multiplying the i-th element of the second component spectrum by the j-th intensity profile element along the value axis of the hypothetical addition rate. This relationship is expressed by the equations shown in FIGS. 17-19, labeled "Math. 1" "Math. 2" and "Math. 3" respectively.

W on the right-hand side of the equation in "Math. 1" is a matrix of M rows and two columns which is made up of column vectors being the first component spectrum and the second component spectrum (the equation in "Math. 2"). H on the right-hand side of the equation in "Math. 1" is a matrix of two rows and N columns which is made up of row vectors being the intensity profile of the first component and the intensity profile of the second component along the value axis of the hypothetical addition rate Cj (the equation in "Math. 3"). The matrix A, described above, was obtained as a result of step S340 in FIG. 3. A method for multivariate analysis, described below, can apply starting from the matrix A to thereby obtain the matrix H and the intensity profile of the second component, which is a row vector of the matrix H. This operation is equivalent to determining a calibration curve in the standard addition method. Thus, it is achievable to find out the unknown concentration of glucose contained in the analysis-target sample 10.

The analytical method performed by the extraction unit 170 is as follows. Initial values of the matrix W are given and the matrix H is approximated from the matrix A and the initial values of the matrix W. Then, the matrix W is approximated from the matrix A and the approximate values of the matrix H. This process is iterated until a predetermined convergence condition is fulfilled, to thereby reach the final approximate values of the matrix H.

As the initial values of the matrix W, for example, the first component spectrum is given a second derivative spectrum of the original spectrum and the second component spectrum is given a second derivative spectrum of the reference spectrum (the number of times differentiation is performed here or the presence or absence of differentiation is assumed to be the same as that when the analysis-target spectra are generated). In addition, the first component intensity profile of the matrix H is derived from the component not targeted for quantification and is thus kept constant without depending on the value of the hypothetical addition rate. The first component intensity profile is thus fixed to a row vector whose elements are all equal to, for example, 1. Under the conditions described above, a computation for minimizing the residual squared norm of the matrices A and W·H, $\|A-W\cdot H\|_2$, with respect to the matrix H (the well-known least-squares method) is performed to enable approximation of the matrix H.

Subsequently, the matrix W is approximated. In the approximation of the matrix W, least-squares approximation with an L1-norm constraint imposed is applied so that the spectrum of the first component may not be affected by the spectrum of the second component (since it should not be affected from the beginning). To this, a mathematically well-known method called LASSO (Least Absolute Shrinkage and Selection Operator) (for example, Toshiyuki TANAKA, "Mathematics of Compressed Sensing", the Institute of Electronics, Information and Communication Engineers (IEICE), Engineering Sciences Society, Fundamentals Review, Vol. 4, No. 1, p. 42, July 2010) can be applied. Specifically, the matrix W is determined so that the value given by the following mathematical expression is minimized at each pixel i.

$$\|A_i - (WH)_i\|_2 + c_{LI}\sum_{k=1}^{2}|w_{ik}|. \quad \text{[Math. 4]}$$

In the above expression, the first term is the residual squared norm of the matrices A and W·H and the second term is the L1-norm of the row vector Wi. The coefficient $C_{L1}$ is a control parameter determined from the accuracy of approximation and the rate of convergence which have a mutual trade-off relationship. Computation in which the sum of the first term and the second term is minimized with respect to the matrix W allows the matrix W to be approximated so that sparseness can hold between the first component spectrum and the second component spectrum. Also in this case, the second component spectrum is given a second derivative spectrum of the reference spectrum Sref (the number of times differentiation is performed here or the presence or absence of differentiation is assumed to be the same as that when the analysis-target spectra are generated). Since the second component spectrum should fundamentally be derived only from a component targeted for quantification, it is appropriate to impose this condition.

As described above, a computation for alternately approximating the matrix H and the matrix W by using least-squares approximation with an L1-norm as a constraint is iterated until a convergence condition that, for example, the residual squared norm of the matrices A and W·H is less than or equal to a predetermined value is fulfilled. This allows the extraction unit 170 to obtain the final approximate values of the matrix H (step S350 in FIG. 3). The second component intensity profile of the matrix H which is determined in the way described above represents a calibration curve determined in a hypothetical fashion and exhibits linear dependence on the hypothetical addition rate.

Figure 8:
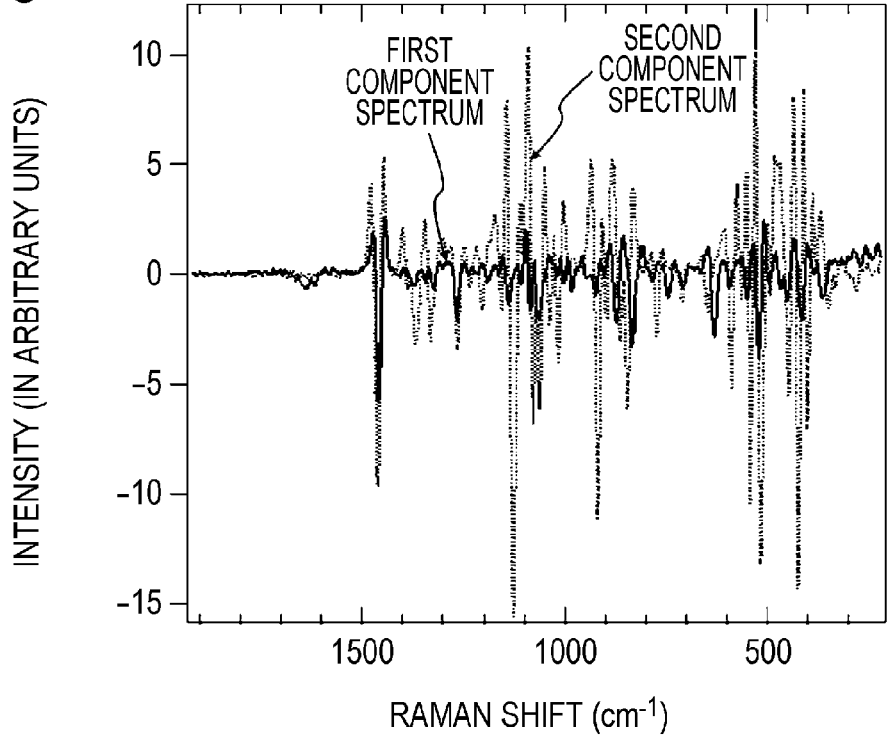
FIG. 8 is a chart illustrating, by way of example, a first component spectrum and a second component spectrum after a convergence condition is fulfilled (Example 1).
Figure 9:
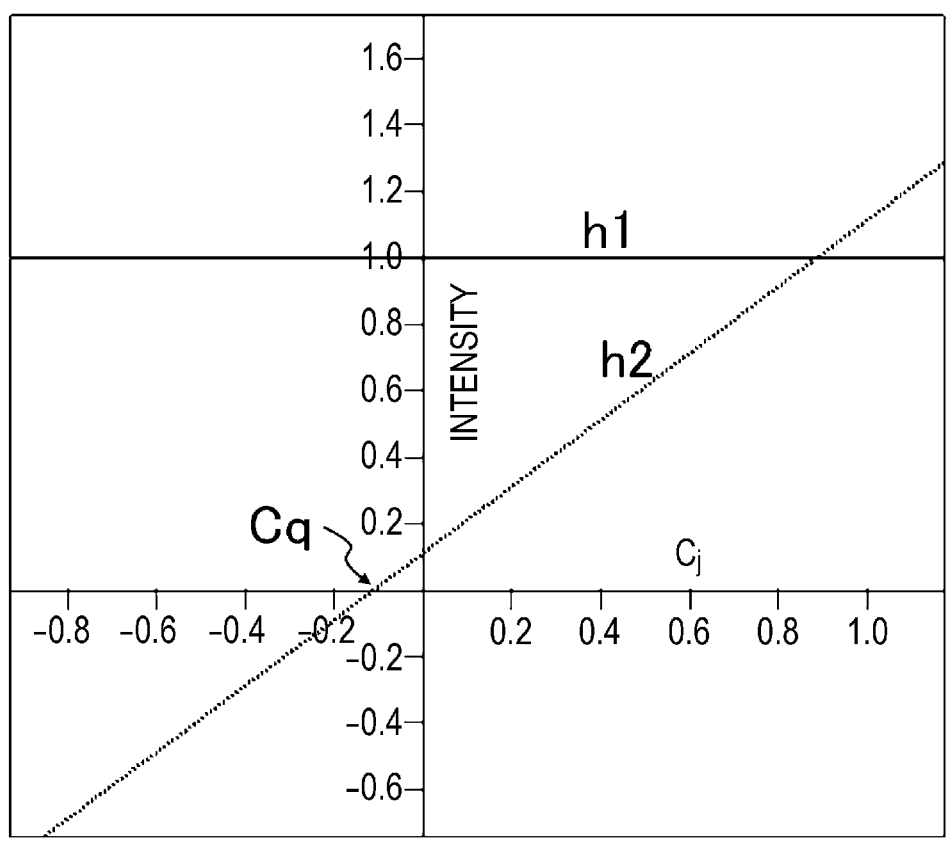
FIG. 9 is a chart illustrating, by way of example, a first component intensity profile and a second component intensity profile after a convergence condition is fulfilled (Example 1).

FIG. 8 is a chart illustrating, by way of example, the first component spectrum (a solid line near an intensity of 0) and the second component spectrum (a dotted line having a larger amplitude) of the matrix W after the convergence condition described above is fulfilled. FIG. 9 illustrates the first component intensity profile (represented by a sign h1) and the second component intensity profile (represented by a sign h2) of the matrix H, which are simultaneously determined by the extraction unit 170 and are input to the determination unit 190. In FIG. 9, the vertical axis and the horizontal axis represent the signal intensity (in arbitrary units) and the hypothetical addition rate Cj, respectively.

The determination unit 190 determines, in a way similar to that when the existing calibration curve is used, the absolute value of a negative hypothetical addition rate (represented by symbol Cq) for which a signal intensity of zero is matched on the straight line representing the first component intensity profile, as the concentration of glucose contained in the analysis-target sample 10, where the concentration of the reference sample is used as a measure. In the example in FIG. 9, Cq=−0.108 and the glucose concentration for the reference sample was 10%. Thus, the determined concentration of glucose is 1.08% (step S360 in FIG. 3). Since the glucose concentration true value with which the analysis-target sample 10 was prepared was 1.05%, the error of the determined unknown concentration in Example 1 is +2.86%.

A spectrum obtained by subtracting a spectrum derived from glucose, which is a component targeted for quantification, from the original spectrum Sorg of the analysis-target sample 10 is represented by Srem. This yields the equation $$Sorg = Srem + |Cq| \times Sref,$$

yielding $$Srem = Sorg + Cq \times Sref \because Cq < 0.$$

In this way, the original spectrum can be decomposed into a spectrum derived from the component targeted for quantification and a spectrum derived from the residual component not targeted for quantification.

Figure 10:
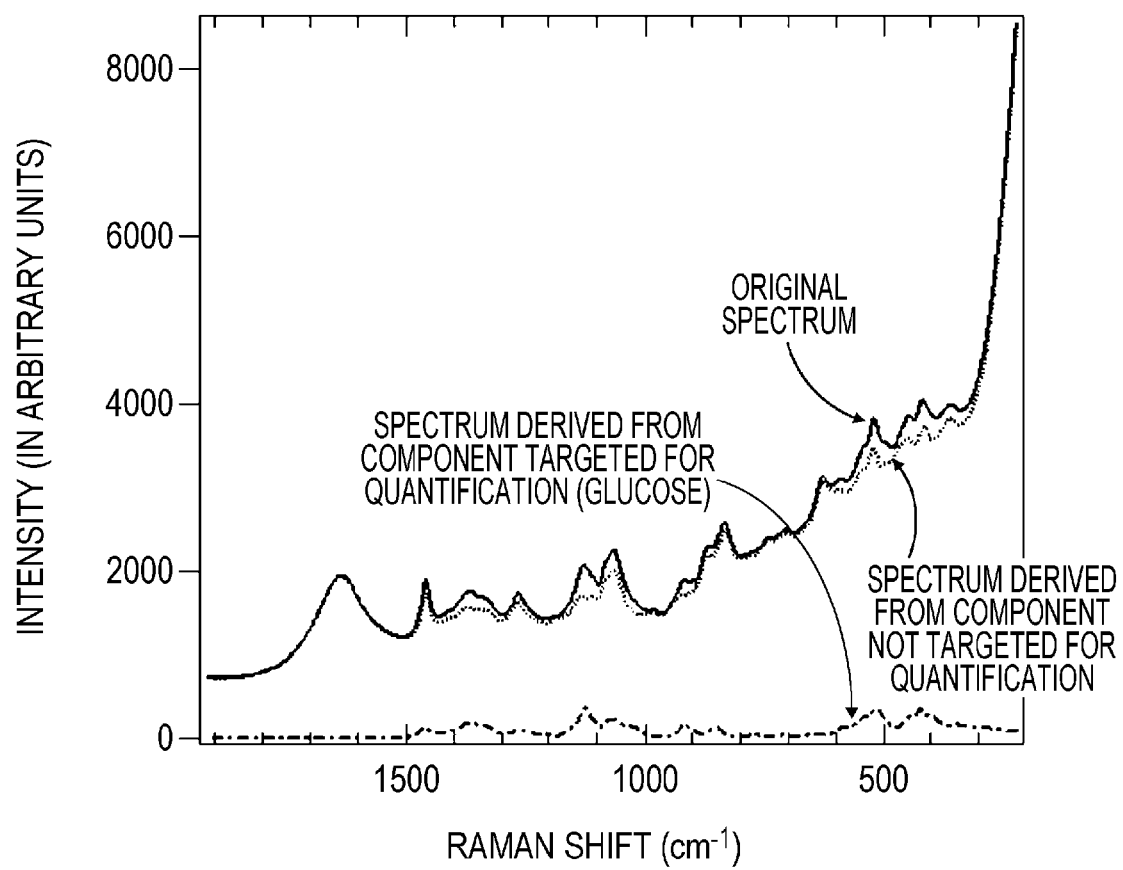
FIG. 10 is a chart illustrating, by way of example, an original spectrum and spectra extracted from the original spectrum, namely, a spectrum derived from a component targeted for quantification and a spectrum derived from a component not targeted for quantification (Example 1).

FIG. 10 illustrates the spectrum derived from the component targeted for quantification and the spectrum derived from the residual component not targeted for quantification, which are obtained as a result of decomposition in the way described above, together with the original spectrum (these spectra being respectively represented by a one-dot chain line, a dotted line, and a solid line). In FIG. 10, the vertical and horizontal axes correspond to those in FIGS. 5 to 8, except for the range of values. FIG. 10 notably depicts the excellent effect of the present invention that it is achievable to extract a spectrum derived from a component targeted for quantification, which has much lower intensity than a spectrum derived from a component not targeted for quantification and which is embedded in the original spectrum.

The convergence condition described above is not limited to the residual squared norm of the matrices A and W·H, and the determination may be based on convergence of the L1-norm of the matrix W or the value of Cq. According to Example 1 of the present invention, an unknown concentration of glucose can be determined with high accuracy from an analysis-target sample that is an aqueous mixed solution of glucose, sucrose, and fructose by using the Raman spectroscopic analysis. While an unknown concentration of one type of component (glucose) was determined in this Example, unknown concentrations of a plurality of types of components can also be determined at a time by performing the method described above on each of the components.

Example 2

Example 2 of the present invention will be described with reference to FIGS. 11 to 14. Example 2 provides enumeration of results of applying a method similar to that in Example 1 to a plurality of other types of mixtures (solutions) by using the same quantitative spectrometry apparatus 100 as that described in Example 1 to determine the concentrations of components targeted for quantification. In the following spectral diagrams, the vertical and horizontal axes correspond to those in FIGS. 5 to 8 and 10, except for the range of values.

Figure 11:
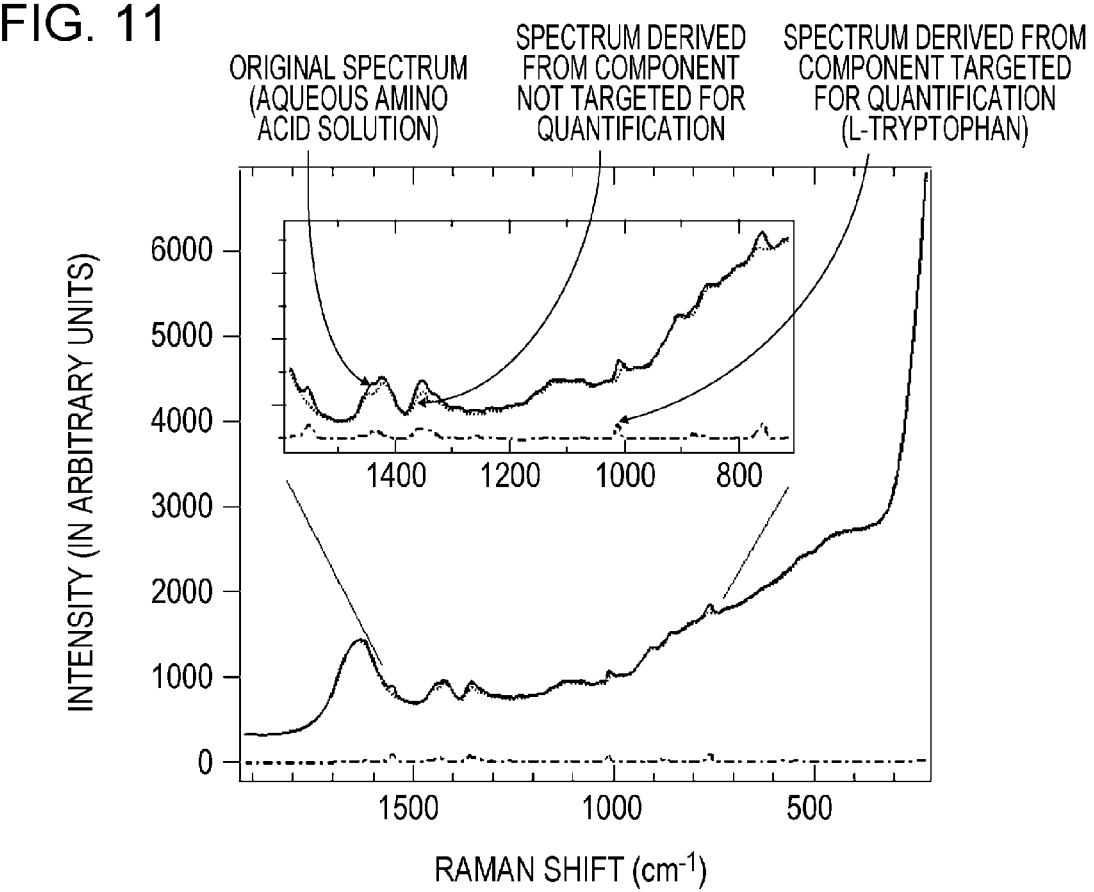
FIG. 11 is a chart illustrating, by way of example, decomposition of spectra based on analysis of an aqueous amino acid solution (Example 2).

FIG. 11 is a diagram illustrating results of analysis using an aqueous amino acid solution as an analysis-target sample (decomposition into a spectrum derived from a component targeted for quantification and a spectrum derived from a component not targeted for quantification). The respective line types representing the individual spectra are distinguishable in the same way as in FIG. 10. Components in the aqueous amino acid solution and the true values of their concentrations are as follows: L-tryptophan (0.96 milligrams (mg)/milliliter (mL)), L-glutamine (9.05 mg/mL), L-asparagine (2.63 mg/mL), and L-arginine (1.15 mg/mL). In FIG. 11, the range of the Raman shift values of 750 to 1600 (cm$^{-1}$) is depicted enlarged in the corresponding inner frame.

Among the components, L-tryptophan was used as a component targeted for quantification and the others were used as components not targeted for quantification. The concentration of the component targeted for quantification was determined by using the Raman spectroscopic analysis in a way similar to that in Example 1. The result was 0.94 mg/mL and the error with respect to the true value is −2.1%.

Figure 12:
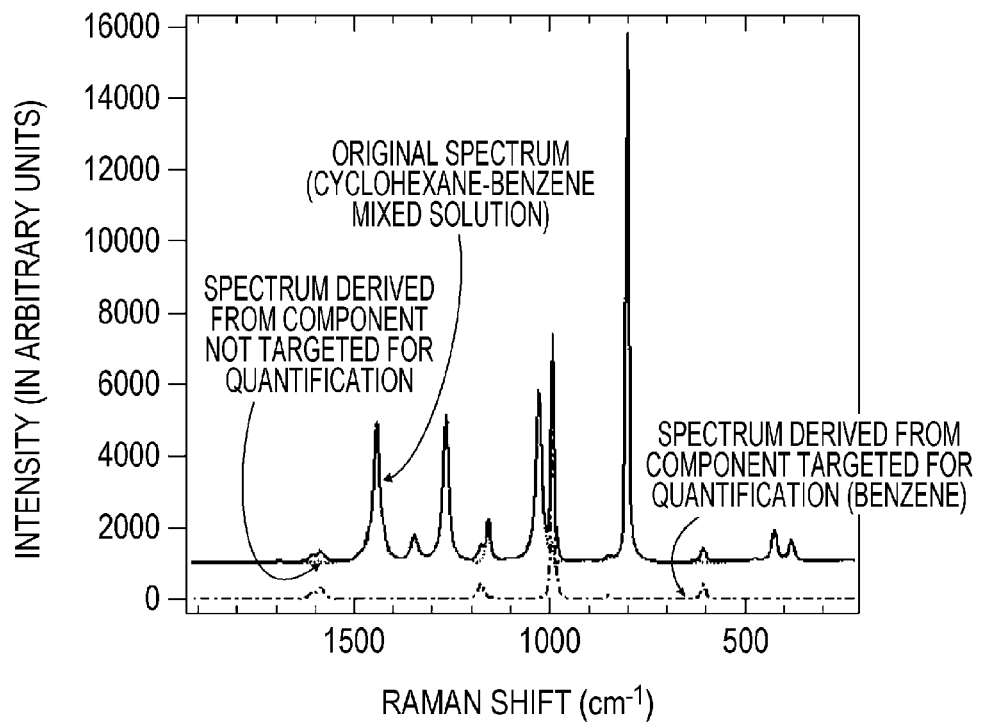
FIG. 12 is a chart illustrating, by way of example, decomposition of spectra based on analysis of a cyclohexane-benzene mixed solution (Example 2).

FIG. 12 is a diagram illustrating results of analysis similar to those in FIG. 11 using a cyclohexane-benzene mixed solution as an analysis-target sample. The respective line types representing the individual spectra are distinguishable in the same way as in FIGS. 10 and 11. The true value of the concentration of benzene, which was used as a component targeted for quantification, is 1.30 moles (mol)/liter (L).

The concentration of benzene, which is a component targeted for quantification, was determined for the mixed solution described above by using the Raman spectroscopic analysis in a manner similar to that in Example 1. The result was 1.21 mol/L and the error with respect to the true value is −6.9%.

Figure 13:
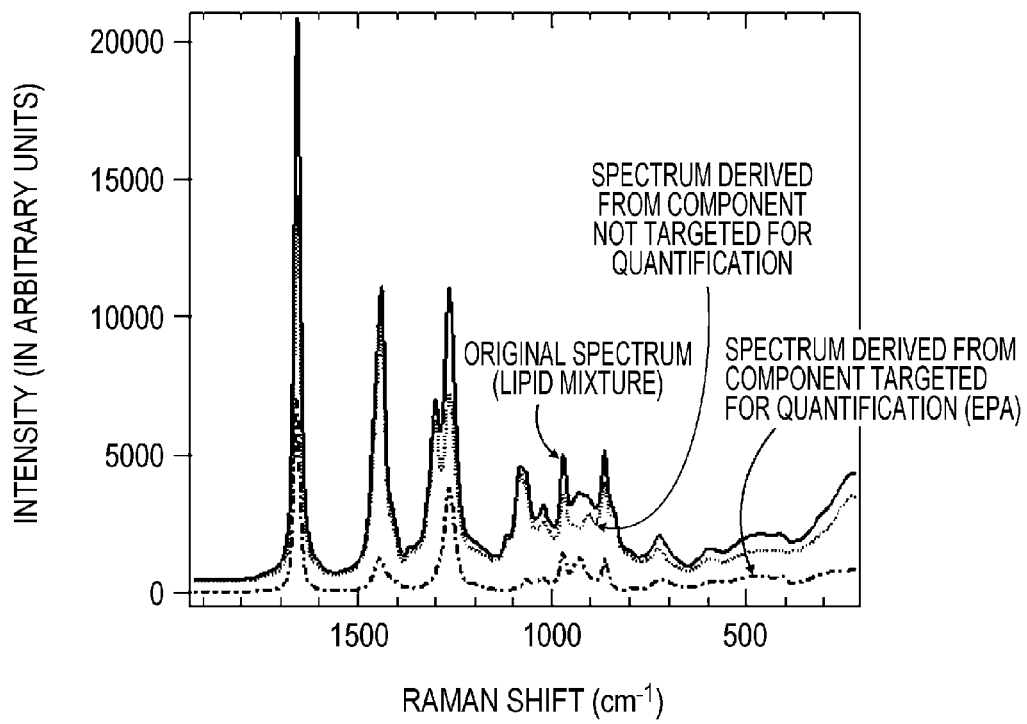
FIG. 13 is a chart illustrating, by way of example, decomposition of spectra based on analysis of a lipid mixture (Example 2).

FIG. 13 is a diagram illustrating results of analysis similar to those in FIG. 11 using a lipid mixture as an analysis-target sample. The respective line types representing the individual spectra are distinguishable in the same way as in FIGS. 10 and 11. Components of the lipid mixture and the true values of their concentrations are as follows: eicosapentaenoic acid (EPA) (148 mg/mL), oleic acid (432 mg/mL), and α-linolenic acid (300 mg/mL).

Among the components, EPA was used as a component targeted for quantification and the others were used as components not targeted for quantification. The concentration of EPA, which is a component targeted for quantification, was determined by using the Raman spectroscopic analysis in a manner similar to that in Example 1. The result was 154 mg/mL and the error with respect to the true value is +4.1%.

Figure 14:
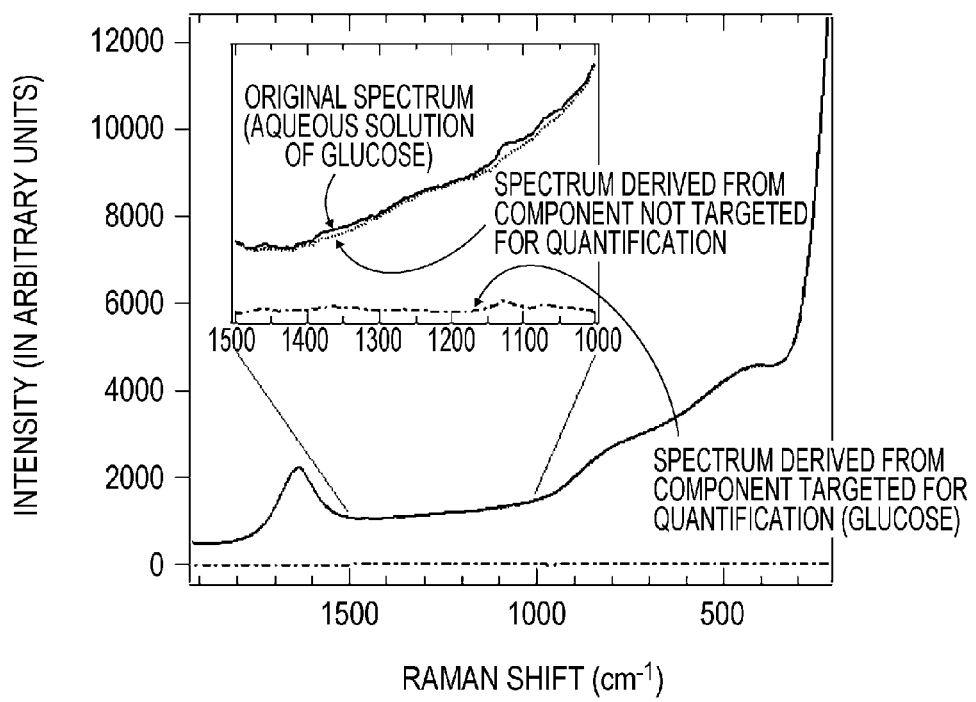
FIG. 14 is a chart illustrating, by way of example, decomposition of spectra based on analysis of an aqueous solution of glucose (Example 2).

FIG. 14 is a diagram illustrating results of analysis similar to those in FIG. 11 using an aqueous solution of glucose as an analysis-target sample. The respective line types representing the individual spectra are distinguishable in the same way as in FIGS. 10 and 11. In FIG. 14, the range of the Raman shift values of 1000 to 1500 (cm$^{-1}$) is depicted enlarged in the corresponding inner frame. The true value of the concentration of glucose, which was used as a component targeted for quantification, is 0.095%. By contrast, the concentration of glucose was determined by using the Raman spectroscopic analysis in a manner similar to that in Example 1. The result was 0.091% and the error with respect to the true value is −4.2%.

According to Example 2, the concentrations of components targeted for quantification in analysis-target samples can be determined with high accuracy by applying the method of the present invention to a plurality of types of mixtures (solutions) different from that in Example 1.

Example 3

Example 3 of the present invention will be described with reference to FIGS. 15 and 16. Example 3 provides enumeration of results of applying a method similar to that in Example 1 to a plurality of other types of mixtures (solids or gases) by using the same quantitative spectrometry apparatus 100 as that described in Example 1 to determine the composition ratios of components targeted for quantification. In the following spectral diagrams, the vertical and horizontal axes correspond to those in FIGS. 5 to 8 and 10, except for the range of values.

Figure 15:
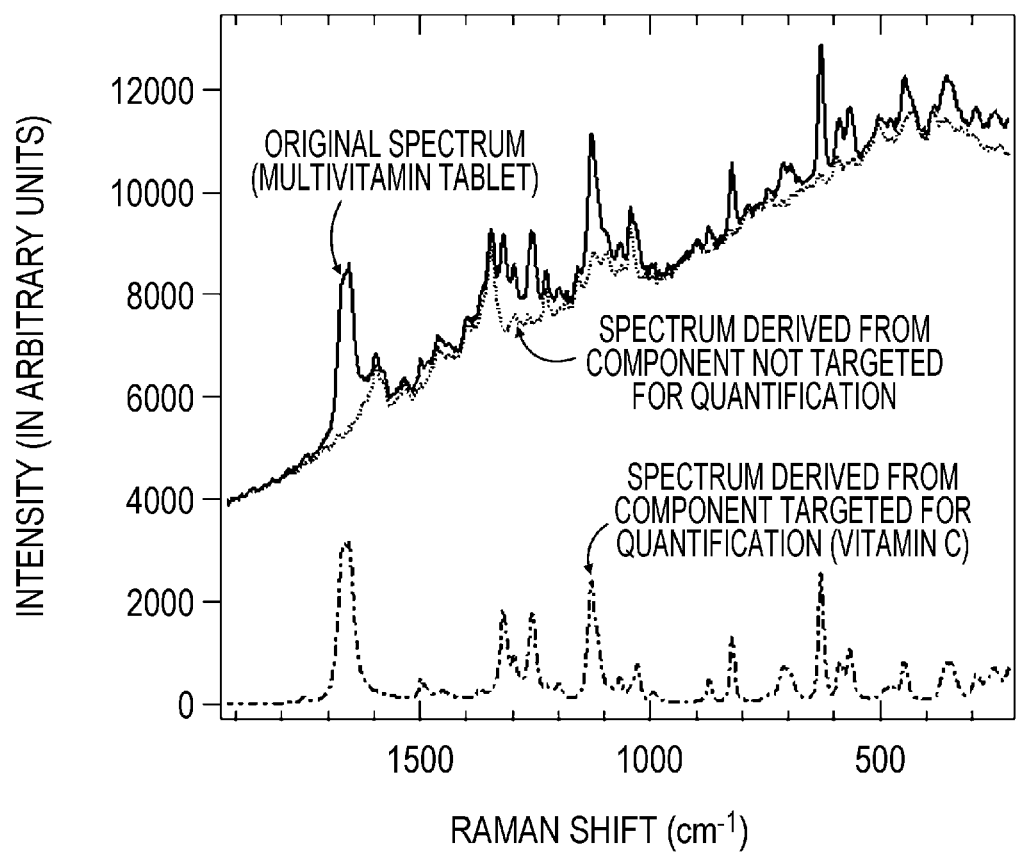
FIG. 15 is a chart illustrating, by way of example, decomposition of spectra based on analysis of a multivitamin tablet (Example 3).

FIG. 15 is a diagram illustrating results of analysis similar to those in FIG. 11 using a multivitamin tablet as an analysis-target sample. The respective line types representing the individual spectra are distinguishable in the same way as in FIGS. 10 and 11. The nominal value of the composition ratio of vitamin C, which was used as a component targeted for quantification, in the tablet is 80 mg per tablet (280 mg).

By contrast, the composition ratio of vitamin C was determined by using the Raman spectroscopic analysis in a manner similar to that in Example 1. In this case, a simulated tablet obtained by mixing vitamin C with starch in a known proportion was used as a reference sample. The determined composition ratio of vitamin C was 79.4 mg per tablet (280 mg), and the error with respect to the true value (which is assumed to be equal to the nominal value) is −0.75%.

Figure 16:
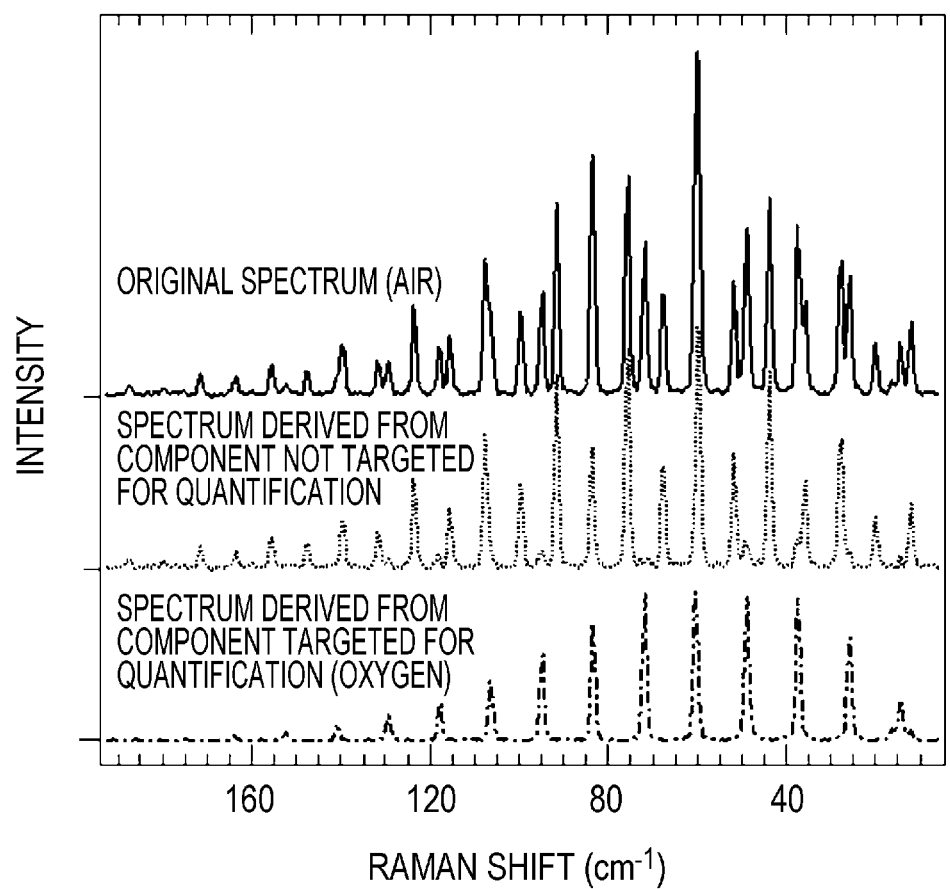
FIG. 16 is a chart illustrating, by way of example, decomposition of spectra based on analysis of air (Example 3).

FIG. 16 is a diagram illustrating results of analysis similar to those in FIG. 11 using air as an analysis-target sample. The respective line types representing the individual spectra are distinguishable in the same way as in FIGS. 10 and 11 (note that offsets with different values are given to the spectral diagrams for consideration of readability of the diagram). The true value of the concentration of oxygen, which was used as a component targeted for quantification, in the air is 20.9%.

By contrast, the oxygen concentration in the air was determined by using the Raman spectroscopic analysis in a manner similar to that in Example 1. In this case, oxygen gas was used as a reference sample. The determined oxygen concentration in the air was 20.5%, and the error with respect to the true value is −1.9%.

According to Example 3, the composition ratio of a component targeted for quantification in an analysis-target sample can be determined with high accuracy by applying the method of the present invention to a solid or gaseous sample. The analysis-target samples and components targeted for quantification provided in the respective Examples described above are illustrative, and the present invention is applicable to analysis of the composition of any mixture.

REFERENCE SIGNS LIST 10 analysis-target sample
110 measurement unit
111 light-receiving unit
112 spectral analysis unit
120 storage unit
130 first generation unit
150 second generation unit
170 extraction unit
190 determination unit

The invention claimed is:

1. A method for quantitative spectrometry capable of quantifying a composition ratio of a component targeted for quantification that is contained in an analysis-target sample by using spectroscopic analysis, the analysis-target sample containing the component targeted for quantification and a component not targeted for quantification, the method comprising:
   measuring, using a measurement unit comprising a light-receiving unit and a spectral analysis unit, an original spectrum from the analysis-target sample by using the spectroscopic analysis, the analysis-target sample containing the component targeted for quantification in an unknown composition ratio, the analysis-target sample being in one of a liquid phase, a solid phase and a gas phase;
   multiplying, using a first generation unit, a reference spectrum by a plurality of hypothetical addition rates which permit any positive and negative values, the reference spectrum being measured by using the spectroscopic analysis from a reference sample containing the component targeted for quantification in a known composition ratio, and adding the respective hypothetical addition rate-multiplied reference spectra to the original spectrum, thereby generating a plurality of hypothetical addition spectra;
   generating, using a second generation unit, a plurality of analysis-target spectra from the plurality of hypothetical addition spectra;
   extracting, using an extraction unit, a signal intensity profile of the component targeted for quantification corresponding to the hypothetical addition rates from the plurality of analysis-target spectra by using multivariate analysis; and
   determining, using a determination unit, the unknown composition ratio of the component targeted for quantification from a dependence of the extracted signal intensity profile on the hypothetical addition rates without changing the composition ratio in the analysis-target sample stepwise.

2. The method for quantitative spectrometry according to claim 1, wherein the reference spectrum is obtained as a difference between a first spectrum measured from the reference sample by using the spectroscopic analysis and a second spectrum measured by using the spectroscopic analysis from a sample obtained by removing the component targeted for quantification from the reference sample.

3. The method for quantitative spectrometry according to claim 1, wherein the plurality of hypothetical addition spectra are used directly as the plurality of analysis-target spectra.

4. The method for quantitative spectrometry according to claim 1, wherein the plurality of analysis-target spectra are generated by performing a differentiation operation on each of the plurality of hypothetical addition spectra one or more times along a spectral axis that is an axis representing a wave number, wavelength, or frequency of light.

5. The method for quantitative spectrometry according to claim 1, wherein the multivariate analysis comprises
   when the analysis-target spectra are decomposed into and represented by a first matrix and a second matrix, the first matrix including a spectrum of the component not targeted for quantification and a spectrum of the component targeted for quantification, the second matrix including a signal intensity profile of the component not targeted for quantification corresponding to the hypothetical addition rates and the signal intensity profile of the component targeted for quantification corresponding to the hypothetical addition rates,
   iterating, while keeping the signal intensity profile of the component not targeted for quantification corresponding to the hypothetical addition rates in the second matrix constant and until a predetermined convergence condition is fulfilled, a computation for alternately determining the first matrix and the second matrix by using least-squares approximation with an L1-norm as a constraint so that the signal intensity profile of the component targeted for quantification corresponding to the hypothetical addition rates has a linear relationship with the hypothetical addition rates and a contribution of the spectrum of the component targeted for quantification to the spectrum of the component not targeted for quantification in the first matrix is made zero.

6. The method for quantitative spectrometry according to claim 1, wherein spectroscopic analysis methods including ultraviolet-visible absorption spectroscopic analysis, fluorescence spectroscopic analysis, phosphorescence spectroscopic analysis, atomic absorption spectroscopic analysis, infrared absorption spectroscopic analysis, Raman spectroscopic analysis, X-ray spectroscopic analysis, nuclear magnetic resonance analysis, electron-spin resonance analysis, and microwave analysis are applicable, in general, as the spectroscopic analysis.

7. The method for quantitative spectrometry according to claim 1, wherein the component targeted for quantification is a solute contained in a solution containing the component not targeted for quantification.

8. The method for quantitative spectrometry according to claim 1, wherein the component targeted for quantification is a component contained in a solid containing the component not targeted for quantification.

9. The method for quantitative spectrometry according to claim 1, wherein the component targeted for quantification is a component contained in a gas containing the component not targeted for quantification.

10. A quantitative spectrometry apparatus for quantifying a composition ratio of a component targeted for quantification that is contained in an analysis-target sample by using spectroscopic analysis, the analysis-target sample containing the component targeted for quantification and a component not targeted for quantification, the quantitative spectrometry apparatus comprising:
a measurement unit for measuring an original spectrum from the analysis-target sample by using the spectroscopic analysis, the analysis-target sample containing the component targeted for quantification in an unknown composition ratio, the analysis-target sample being in one of a liquid phase, a solid phase and a gas phase;
a first generation unit for multiplying a reference spectrum by a plurality of hypothetical addition rates which permit any positive and negative values, the reference spectrum being measured by using the spectroscopic analysis from a reference sample containing the component targeted for quantification in a known composition ratio, and adding the respective hypothetical addition rate-multiplied reference spectra to the original spectrum, thereby generating a plurality of hypothetical addition spectra;
a second generation unit for generating a plurality of analysis-target spectra from the plurality of hypothetical addition spectra;
an extraction unit for extracting a signal intensity profile of the component targeted for quantification corresponding to the hypothetical addition rates from the plurality of analysis-target spectra by using multivariate analysis; and
a determination unit for determining the unknown composition ratio of the component targeted for quantification from a dependence of the extracted signal intensity profile on the hypothetical addition rates without changing the composition ratio in the analysis-target sample stepwise.

11. The quantitative spectrometry apparatus according to claim 10, wherein the measurement unit is further capable of obtaining the reference spectrum as a difference between a first spectrum measured from the reference sample by using the spectroscopic analysis and a second spectrum measured by using the spectroscopic analysis from a sample obtained by removing the component targeted for quantification from the reference sample.

12. The quantitative spectrometry apparatus according to claim 11, further comprising a storage unit capable of storing data of the reference spectrum obtained by the measurement unit.

13. The quantitative spectrometry apparatus according to claim 10, wherein the second generation unit is capable of using the plurality of hypothetical addition spectra directly as the plurality of analysis-target spectra.

14. The quantitative spectrometry apparatus according to claim 10, wherein the second generation unit is capable of generating the plurality of analysis-target spectra by performing a differentiation operation on each of the plurality of hypothetical addition spectra one or more times along a spectral axis that is an axis representing a wave number, wavelength, or frequency of light.

15. The quantitative spectrometry apparatus according to claim 10, wherein the extraction unit is capable of performing the multivariate analysis by,
when the analysis-target spectra are decomposed into and represented by a first matrix and a second matrix, the first matrix including a spectrum of the component not targeted for quantification and a spectrum of the component targeted for quantification, the second matrix including a signal intensity profile of the component not targeted for quantification corresponding to the hypothetical addition rates and the signal intensity profile of the component targeted for quantification corresponding to the hypothetical addition rates,
iterating, while keeping the signal intensity profile of the component not targeted for quantification corresponding to the hypothetical addition rates in the second matrix constant and until a predetermined convergence condition is fulfilled, a computation for alternately determining the first matrix and the second matrix by using least-squares approximation with an L1-norm as a constraint so that the signal intensity profile of the component targeted for quantification corresponding to the hypothetical addition rates has a linear relationship with the hypothetical addition rates and a contribution of the spectrum of the component targeted for quantification to the spectrum of the component not targeted for quantification in the first matrix is made zero.

16. The quantitative spectrometry apparatus according to claim 10, wherein spectroscopic analysis methods including ultraviolet-visible absorption spectroscopic analysis, fluorescence spectroscopic analysis, phosphorescence spectroscopic analysis, atomic absorption spectroscopic analysis, infrared absorption spectroscopic analysis, Raman spectroscopic analysis, X-ray spectroscopic analysis, nuclear magnetic resonance analysis, electron-spin resonance analysis, and microwave analysis are applicable, in general, as the spectroscopic analysis.

17. The quantitative spectrometry apparatus according to claim 10, wherein the component targeted for quantification is a solute contained in a solution containing the component not targeted for quantification.

18. The quantitative spectrometry apparatus according to claim 10, wherein the component targeted for quantification is a component contained in a solid containing the component not targeted for quantification.

19. The quantitative spectrometry apparatus according to claim 10, wherein the component targeted for quantification is a component contained in a gas containing the component not targeted for quantification.

20. A program embedded in a non-transitory computer readable medium for causing a computer to perform a process for quantifying a composition ratio of a component targeted for quantification that is contained in an analysis-target sample by using spectroscopic analysis, the analysis-target sample containing the component targeted for quantification and a component not targeted for quantification, the program comprising:

receiving data input of a reference spectrum measured from a reference sample by using the spectroscopic analysis, the reference sample containing the component targeted for quantification in a known composition ratio;

receiving data input of an original spectrum measured from the analysis-target sample by using the spectroscopic analysis, the analysis-target sample containing the component targeted for quantification in an unknown composition ratio, the analysis-target sample being in one of a liquid phase, a solid phase and a gas phase;

executing a process of multiplying the reference spectrum by a plurality of hypothetical addition rates which permit any positive and negative values and adding the respective hypothetical addition rate-multiplied reference spectra to the original spectrum, thereby generating a plurality of hypothetical addition spectra;

executing a process of generating a plurality of analysis-target spectra from the plurality of hypothetical addition spectra;

executing a process of extracting a signal intensity profile of the component targeted for quantification corresponding to the hypothetical addition rates from the plurality of analysis-target spectra by using multivariate analysis; and executing a process of determining the unknown composition ratio of the component targeted for quantification from a dependence of the extracted signal intensity profile on the hypothetical addition rates without changing the composition ratio in the analysis-target sample stepwise.

* * * * *